United States Patent [19]

Dermeik et al.

[11] Patent Number: 5,648,509

[45] Date of Patent: Jul. 15, 1997

[54] PROCESS FOR THE PREPARATION OF DIESTERS OF PHOSPHONOCARBOXYLIC ACID DERIVATIVES

[75] Inventors: Salman Dermeik, Augsburg; Martina Wanner, Neusäss; Karl-Heinz Lemmer, Augsburg; Reinhold Braun, Schwabmünchen, all of Germany

[73] Assignee: Ciba-Geigy Corporation, Tarrytown, N.Y.

[21] Appl. No.: 508,145

[22] Filed: Jul. 27, 1995

[30] Foreign Application Priority Data

Jul. 29, 1994 [DE] Germany .......................... 44 26 986.2
Feb. 3, 1995 [DE] Germany .......................... 195 03 518.6

[51] Int. Cl.$^6$ ....................................................... C07F 9/02
[52] U.S. Cl. ............................. 558/137; 558/145; 558/87
[58] Field of Search ................................. 558/137, 145, 558/87

[56] References Cited

U.S. PATENT DOCUMENTS

| | | | |
|---|---|---|---|
| 2,754,319 | 7/1956 | Johnston | 260/461 |
| 2,754,320 | 7/1956 | Johnston et al. | 260/461 |
| 2,844,558 | 7/1958 | Toy et al. | 260/45.4 |
| 2,971,019 | 2/1961 | Ladd et al. | 260/461 |
| 3,699,192 | 10/1972 | Marotti | 260/926 |

FOREIGN PATENT DOCUMENTS 1130222 2/1957 France.

OTHER PUBLICATIONS

Yankov et al., Dokl. Bolg. Akad. Nauk 42(12), 75–7 (1989).
Wasielewski et al., J. Prakt. Chem., 331(3), 507–10 (1989).
Zhao et al., Phosphorus Sulfur, 33(1–2), 53–9 (1987).
Mahran et al., Heteroat. Chem., 3(2), 93–9 (1992).
Chem. Abstract, vol. 102, #23 (1985) 204043, Makosza et al.
Comptes rendus de L'Académie bulgare des Sciences, 42, No. 12, 1989, pp. 75–77.

*Primary Examiner*—Johann Richter
*Assistant Examiner*—Laura R. Cross
*Attorney, Agent, or Firm*—Kevin T. Mansfield

[57] ABSTRACT

The addition of acid diesters of phosphorous acid onto alpha,beta-unsaturated carboxylic acid derivatives under basic catalysis is achieved with good yields if it is carried out in the presence of alkali metal alcoholates or phenolates and in the presence of halides, oxides or hydroxides of divalent metals. Co-use of these metal compounds allows relatively small mounts of metal alcoholates or phenolates to be used. The resulting reaction mixtures do not contain relatively large amounts of troublesome by-products.

8 Claims, No Drawings

PROCESS FOR THE PREPARATION OF DIESTERS OF PHOSPHONOCARBOXYLIC ACID DERIVATIVES

The invention relates to a process for the preparation of phosphono compounds of the formula (I)

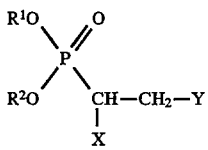
(I)

by reaction of a phosphite of the formula (II)

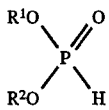
(II)

with a compound containing a carbon-carbon double bond, of the formula (III)

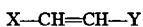
(III)

in which $R^1$ and $R^2$, independently of one another, are a phenyl radical or alkyl radical having 1 to 4 carbon atoms which is optionally substituted by one or more chlorine or bromine atoms, in which X is hydrogen or a methyl group and in which Y is —$COOR^1$, —$CONH_2$, —$CONHR^1$, —$CONR^1_2$ or —C≡N, where $R^1$ has the abovementioned meaning.

Processes of the type mentioned are known, for example, from U.S. Pat. Nos. 3,699,192, 2,971,019 and U.S. Pat. No. 2,754,320. Similar processes are furthermore described in U.S. Pat. No. 2,754,319. In addition, "Comptes rendus de l'Académie bulgare des Sciences", Volume 42, No. 12, 1989, pages 75 to 77 also relates to processes of the abovementioned type. It can also be seen from the latter publication that the addition of dialkyl phosphites onto alpha,beta-unsaturated carboxamides can be readily catalyzed by sodium alcoholate. U.S. Pat. No. 2,971,019 describes a process of the abovementioned type which is carried out in the presence of a basic compound. A number of suitable basic compounds are disclosed in the specification. However, it is not suggested to the expert to employ more than one basic compound for carrying out the process.

The reaction products of the formula (I) obtained by the process mentioned, that is to say diesters of phosphonocarboxylic acid derivatives, can be used in the flameproofing sector. For example, they can be employed as starting materials for the preparation of products which are known from the technical literature and are used in the form of aqueous dispersions for providing fiber materials, such as woven fabrics or mesh goods, with a flame-retardant finish.

The processes known from the abovementioned publications for addition of phosphites onto activated carbon-carbon double bonds in the presence of basic catalysts have disadvantages. It has thus been found that the yields of the desired addition product and the amounts of undesirable by-products present in the reaction mixture depend on the nature and/or amount of the catalyst chosen. The basic catalysts used in known processes can react with starting compounds to give undesirable by-products. Alkali metal alcoholates or phenolates have proven to be the most favorable of the known basic catalysts for achieving high yields of the desired addition product. However, undesirable side reactions can also occur even when these are used, leading to some of the amount of catalyst employed thereby being consumed and the yield of the desired addition product falling. The consequence of this is that in the processes known from the prior art, in order to achieve good yields and acceptable rates of reaction, higher amounts of catalyst than would be necessary for catalysis of the addition of the phosphite onto the carbon-carbon double bond of the compound of the formula (III) must be employed. This increase in the amount of catalyst makes the process more expensive. In addition, it also includes another disadvantage. For handling reasons, in particular, the alkali metal alcoholates often used as catalysts are preferably employed in the form of a solution in the corresponding alcohol, for example in the form of a solution of sodium methylate in methanol. In this case, an increase in the amount of catalyst means an increase in the methanol content in the reaction product. Removal of the methanol from the reaction product or from a secondary product thereof by distillation is slowed down and made more expensive due to the increased amount. A secondary reaction between the basic catalyst and one of the starting compounds, such as usually occurs in known processes, furthermore means that unreacted portions of the other starting compound remain in the reaction mixture if equivalent amounts of compounds of the formulae (II) and (III) have been employed. However, under certain circumstances unreacted portions of one of the two starting compounds in the reaction mixture are highly undesirable. In order to avoid them or to reduce them to a very low level, the known processes must be carried out with a not inconsiderable excess of the other starting compound. This makes the process more expensive on the one hand, and on the other hand can lead to an undesirably high content of by-products which are formed by side reactions with the participation of the components present in excess and of basic catalyst, for example metal alcoholate.

Another disadvantage of the known processes for addition of phosphites onto activated carbon-carbon double bonds has emerged in the case where the reaction is carried out only in the presence of an oxide or hydroxide of a divalent metal, that is to say without addition of a metal alcoholate or phenolate. In order to achieve a reaction time which is acceptable in practice, a relatively high amount of oxide or hydroxide of the metal must be used in this case and the reaction mixture must be heated to a relatively high temperature. However, as soon as the reaction has been started, this can be controlled only with difficulty because of the relatively high amount of oxide or hydroxide and because of the exothermicity.

The present invention was therefore based on the object of developing an improved process for addition of phosphorous acid diesters (acid phosphites) of the formula (II) onto alpha,beta-unsaturated carboxylic acid derivatives of the formula (III), in particular a process in which smaller amounts of strongly basic catalysts, such as alkali metal alcoholates or phenolates, are required than in known processes, which can be carded out with equivalent or approximately equivalent amounts of the starting substances of the formulae II and III, and which nevertheless has acceptable rates of reaction and leads to good yields of the desired reaction product and only small amounts of by-products.

The object was achieved by a process of the type mentioned above and in claim 1, in which the reaction is carried out both in the presence of a basic catalyst of the formula $MOR^1$, in which M is an alkali metal, preferably Na or K, and $R^1$ has the meaning given above and in claim 1, in which $R^1$ in the formula $MOR^1$ is preferably an unsubstituted alkyl radical, in particular the methyl or ethyl group, and in the presence of a halide, oxide or hydroxide of a divalent metal.

The process according to the invention has the following advantages:

1. The amount of metal alcoholate or phenolate serving as the strongly basic catalyst can be kept considerably lower than the amount required in known processes, often by a factor of 10. The process thereby becomes cheaper. The content of this strongly basic catalyst may be even lower, depending on the nature of the reaction conditions chosen. The amount of this strongly basic catalyst used is preferably lower than in known processes, for example lower by a factor of 5 to 10. Attempts to use similarly low amounts of strongly basic catalysts in known processes, that is to say without addition of halides, oxides or hydroxides of divalent metals, led to poor yields and a high content of unreacted starting compounds in the reaction product because of the formation of by-products and consumption of some of the catalyst. In the process according to the invention, on the other hand, yields of the desired addition product (formula (I)) which are just as high as or yields which are even higher than in known processes can also be achieved using significantly smaller amounts of alkali metal alcoholates or phenolates as strongly basic catalysts.

2. The possibility provided by the process according to the invention of using a smaller amount of strongly basic catalysts (alcoholates or phenolates) known from the prior art has the effect of greatly reducing the formation of by-products with which, as a result of their formation, because of a reaction of this catalyst with one of the starting compounds, some of this starting compound is consumed in known processes. In the process according to the invention, it is therefore possible to keep the amount of unreacted starting substances in the reaction product low without having to employ a larger excess of one of the starting compounds. The decrease in the excess of one starting compound required in known processes leads to a price advantage over known processes and to smaller amounts of undesirable by-products being present in the reaction mixture.

3. In the case where the alkali metal alcoholate or phenolate serving as the basic catalyst is employed in the form of a solution, a reduction in the amount of this catalyst and therefore of the solvent means a reduction in the expenditure in terms of costs and work during later removal of the solvent. One example is the use of a solution of sodium methylate in methanol and later distillation to remove the methanol.

4. Carrying out the process for addition of phosphites onto activated carbon-carbon double bonds in the presence of an oxide or hydroxide of a divalent metal and in the presence of small amounts of a basic catalyst of the formula MOR¹ allows a more easily controllable and reliable reaction of the starting compounds in a reaction time which is acceptable in practice, compared with a process which is carried out only in the presence of an oxide or hydroxide of a divalent metal, that is to say without a basic catalyst of the formula MOR¹.

The process according to the invention will now be described in detail.

In the process, a phosphite of the formula (II)

is reacted with a compound of the formula (III)

$$X-CH=CH-Y \qquad (III).$$

In these formulae, $R^1$ and $R^2$, independently of one another, are a phenyl radical or a saturated alkyl radical having 1 to 4 carbon atoms. Both the phenyl radical and the alkyl radicals can be unsubstituted or have one or more chlorine or bromine atoms as substituents. Phosphites in which $R^1$ and $R^2$, independently of one another, are a methyl or ethyl group, for example dimethyl or diethyl phosphite, are employed as preferred compounds of the formula (II). Suitable phosphites of the formula (II) are commercially available products.

In the abovementioned formula (III), X is hydrogen or a methyl group, preferably hydrogen. Y in formula (III) is one of the following monovalent radicals: —COOR¹, —CONH₂, —CONHR¹, —CONR¹₂ or —C≡N, in which $R^1$ has the abovementioned meaning and is preferably a methyl or ethyl group. The compounds of the formula (III) are accordingly alpha,beta-unsaturated carboxylic esters, amides or nitriles. The compounds of the formula (III) are also generally known, commercially available products. A compound of the formula (III) which is particularly suitable for the process according to the invention is acrylamide.

As already mentioned, the process according to the invention must be carried out in the presence of a strongly basic catalyst of the formula MOR¹.

The strongly basic catalyst of the formula MOR¹ required for the process according to the invention can be chosen from known compounds which are already described in the literature for addition of phosphites of the formula (II) onto compounds of the formula (III). M here is an alkali metal, preferably sodium or potassium. $R^1$ has the meaning given above and in claim 1, and $R^1$ is preferably an unsubstituted alkyl radical having 1 to 4 carbon atoms, in particular a methyl or ethyl group. It is favorable if the radical $R^1$ in the metal alcoholate chosen is the same as that present in the phosphite of the formula (II) used. This means that, in the case of dimethyl phosphite as the starting compound, sodium methylate or potassium methylate is preferably employed as the catalyst.

According to claim 1, the reaction of a phosphite of the formula (II) with a compound of the formula (III) is carried out in the presence of a halide, oxide or hydroxide of a divalent metal. It has been found, surprisingly, that the addition of such a metal compound allows the amount of alcoholate or phenolate as the strongly basic catalyst additionally used to be reduced significantly without reducing the yield of the desired addition product. The advantages of this measure are described above.

Chlorides or bromides are preferably employed as halides of divalent metals. The halides, oxides or hydroxides of divalent metals are preferably corresponding compounds of alkaline earth metals. Particularly good results are achieved when magnesium chloride, calcium oxide, calcium hydroxide, magnesium oxide or magnesium hydroxide is used.

In the normal case, the process according to the invention is carried out by a procedure in which first the halide, oxide or hydroxide of a divalent metal and then the strongly basic catalyst (alkali metal alcoholate or phenolate) are added to the reaction mixture.

The reaction carried out in the process according to the invention can be carried out in a solvent, for example an alcohol having 1 to 3 carbon atoms. Water is less preferred as the reaction medium. Rather, a preferred embodiment of the process according to the invention comprises a procedure in which all the starting compounds used for the reaction are anhydrous or essentially anhydrous. The halides, oxides or hydroxides of divalent metals used are also preferably completely or essentially anhydrous, that is to say preferably contain no water of crystallization. In a number of cases it may be desirable for the reaction product formed in-the process according to the invention to contain little or no solvent. To achieve this, the reaction can be carried out with the essentially solvent-free compounds of the formulae (II) and (III) and the solid halide, oxide or hydroxide of the divalent metal without addition of a solvent. For easier handling, however, it is also often expedient in this case for the alkali metal alcoholate or phenolate used as the strongly basic catalyst to be employed as a solution in a solvent, for example alcohol, and that alcohol from which the alcoholate in question is derived is expediently used as the solvent.

Instead of a single halide, oxide or hydroxide of a divalent metal, a mixture of such compounds can also be used.

Under certain reaction conditions, the case may occur where polymerization of some of the compound X—CH=CH—Y takes place as an undesirable side reaction. This polymerization can in many cases be suppressed by addition of an inhibitor. Suitable inhibitors are, for example, copper salts or phenols or substituted phenols. Addition of an inhibitor in even the ppm range can be sufficient, depending on the conditions of the reaction.

As already mentioned, the process according to the invention can be carried out with smaller amounts of strongly basic catalyst than processes known from the prior art. The extent of side reactions is thereby suppressed, and it is possible to employ the starting compounds of the formulae (II) and (III) in equivalent or virtually equivalent amounts. This avoids one of the starting compounds still being present in the reaction product in unreacted form in relatively large amounts. A preferred embodiment of the process according to the invention therefore comprises using 0.95 to 1.07, in particular 1.01 to 1.05, mol of phosphite of the formula (II) per mole of compound of the formula (III), for example per mole of acrylamide, for the reaction. These quantifies relate to anhydrous and solvent-free products. If relatively large amounts of unreacted starting compounds in the reaction mixture containing the phosphono compound of the formula (I) cause no trouble, larger deviations from equivalent amounts of starting compounds can also be employed, for example 20% more or less than the equivalent amount of one of the starting compounds of the formula (II) or (III).

It is furthermore preferable to carry out the reaction such that 0.01 to 0.1, in particular 0.015 to 0.05, mol of basic catalyst of the formula $MOR^1$ and either 0.001 to 0.05, in particular 0.003 to 0.015, mol of a halide of a divalent metal or 0.001 to 0.15, in particular 0.02 to 0.08, mol of an oxide or hydroxide of a divalent metal are employed per mole of compound of the formula (III). All these quantities relate to anhydrous and solvent-free products.

It has been found that advantages compared with known processes can already be achieved with 0.001 to 0.05 mol of a halide of a divalent metal or 0.001 to 0.15 mol of an oxide or hydroxide of a divalent metal, in each case per mole of compound of the formula (III). If desired, higher mounts, for example up to 0.1 mol of the halide or up to 0.3 mol of the oxide or hydroxide per mole of compound of the formula (III), can also be used. Increasing the mount of halide above 0.1 mol or the amount of oxide or hydroxide above 0.3 mol may possibly be undesirable because of the larger amount of this halide, oxide or hydroxide thereby present in the reaction product. Particularly good results are achieved if 0.003 to 0.015 tool of halide of a divalent metal or 0.02 to 0.08 mol of an oxide or hydroxide of a divalent metal per mole of compound of the formula (III) are used for the reaction.

The reaction carried out in the process according to the invention can be carried out without an inert gas in air or, if desired, can be carried out in an atmosphere of lower oxygen content and higher nitrogen content than present in air. In some cases, it has proved advantageous to carry out most of the reaction, that is to say until about 90% of the reaction has taken place, in air and then to complete the reaction under an inert gas.

The process according to the invention is preferably carried out at a temperature in the range of 45°–80° C., in particular in the range of 45°–65° C. Because of the exothermic character of the reaction carried out using alkaline compounds, it may be necessary to cool the mixture during the reaction or during part of the reaction in order to carry out the reaction in the temperature range mentioned.

A particularly suitable method of carrying out the process according to the invention comprises initially introducing phosphite of the formula (II), a compound X—CH=CH—Y of the formula (III) and a halide, oxide or hydroxide of a divalent metal, in particular an alkaline earth metal, into a suitable reaction vessel and slowly adding a solution of an alkali metal alcoholate in an alcohol dropwise. The reaction mixture here should be kept at a temperature in the range of 45°–80° C., preferably 45°–65° C., for example by means of cooling and while stirring. When the addition of the solution of the alcoholate has ended, stirring is continued until the reaction has ended, which can take a few minutes to several hours in the normal case. If the reaction mixture obtained after the reaction is not clear but shows clouding, a filtration step can be carried out before the further processing.

If desired, the reaction product of the formula (I) obtained in the process according to the invention can be isolated, purified, for example by means of recrystallization, if appropriate and used for the proposed intended use. It can also serve as a starting substance for secondary products, for example products which can be obtained by methylolation of the compound of the formula (I) by means of formaldehyde or paraformaldehyde in the case where Y in formula (I) is —$CONH_2$ or —$CONHR^1$. These methylolated products are excellent substances for providing fiber materials, such as textiles, with a flame-retardant finish. They are often employed for this purpose in the form of aqueous dispersions which, in addition to compounds of the formula (I), can also comprise other products used for the treatment of fiber materials. It has been found that if suitable conditions have been chosen for the process according to the invention, subsequent methylolation can be carried out directly with the resulting reaction mixture without addition of a further catalyst.

The further reaction of compounds of the formula (I) which may be desired, for example with formaldehyde or paraformaldehyde to give N-methylol compounds (in the case where Y=—$CONH_2$ or —$CONHR^1$) can be carried out in the normal case without the compound of the formula (I) being isolated. That is to say, it is normally possible for the addition products of the formula (I) formed, in which Y is —$CONH_2$ or —$CONHR^1$, to be methylolated directly after the process according to the invention has been carried out, if appropriate after a solvent has also been added. This methylolation can be carried out by methods known from the prior art, for example as described in U.S. Pat. No. 3,374,292. For example, this methylolation can be carried out using basic catalysts, such as metal alcoholates, metal oxides or metal hydroxides. Possible oxides or hydroxides here are the corresponding compounds of alkali metals or alkaline earth metals.

The invention will now be illustrated by embodiment examples.

Example 1 (comparison example not according to the invention)

113.3 g (1.03 mol) of dimethyl phosphite were heated to 40° C. 71 g (1.0 mol) of acrylamide were added at this temperature and the mixture was kept at 30° C. When the acrylamide had dissolved completely, 1.80 g of a 30% strength solution of sodium methylate in methanol (corresponding to 0.01 mol of NaOCH$_3$) were slowly added dropwise in the course of 4 hours. During this period of 4 hours, the temperature in the reaction mixture was kept at about 45° C.–50° C. Stirring was then continued at 50° C. for about a further 15 minutes.

Examples 2 and 3 (comparison examples not according to the invention)

Example 1 was repeated with the difference that not 1.80 g of sodium methylate solution but 9.0 g (Example 2) or 18.01 g (Example 3) were added dropwise in the course of 4 hours.

Example 4 (according to the invention)

Example 1 was repeated with the difference that, after the acrylamide had dissolved, 0.48 g (0.005 mol) of solid anhydrous magnesium chloride was added. The resulting mixture was stirred at 30° C. until a clear solution had formed. The sodium methylate solution was then added dropwise as described in Example 1.

Examples 5 and 6 (examples according to the invention)

The procedure was as in Example 4, with the difference that not 1.80 g of sodium methylate solution but 9.0 g (Example 5) or 18.01 g (Example 6) were used.

The content of free acrylamide and of addition product in each of the reaction mixtures obtained in Examples 1 to 6 was determined by means of high pressure liquid chromatography (HPLC). The addition product corresponds to the formula (I) given above and in claim 1, where $R^1=R^2=CH_3$, X=H and Y=—CONH$_2$.

The results obtained are shown in the following table:

| Example No. | Content of addition product (%) | Content of free acrylamide (%) | Yield of addition product (%) |
| --- | --- | --- | --- |
| 1 | 2.4 | 36.8 | 2.3 |
| 2 | 85.8 | 1.43 | 92.7 |
| 3 | 81.2 | 0.63 | 91.8 |
| 4 | 57.0 | 11.6 | 58.8 |
| 5 | 87.0 | 0.04 | 94.3 |
| 6 | 85.0 | 0.01 | 96.3 |

The values for the content given in the above table are % by weight, based on the total amount of reaction product. The values in the column "Yield of addition product %" indicate the yield of addition product determined, based on the maximum yield theoretically possible.

The results show that an increase in the amount of NaOCH$_3$ under otherwise the same conditions leads to better results. They also show that the addition of magnesium chloride with the same amount of NaOCH$_3$ leads to an increase in the yield of addition product and to a reduction in the amount of free acrylamide in the end product. This finding applies regardless of the amount of catalyst (sodium methylate) employed, as the comparison between Example 1 and 4, between Example 2 and 5 and between Example 3 and 6 shows. A comparison between Example 3 and Example 5 furthermore shows that, if magnesium chloride is added, better results are obtained even with 0.05 mol of NaOCH$_3$ (Example 5) than with 0.1 tool of NaOCH$_3$ without addition of MgCl$_2$ (Example 3).

Example 7 (according to the invention)

540.7 g (4.815 mol) of dimethyl phosphite, 320 g of acrylamide (4.5 mol) and 10 g (0.18 mol) of solid CaO were initially introduced into a reaction vessel and heated up to 65° C. The mixture was stirred at 65° C. for a further 2 hours and then cooled to an internal temperature of 55° C., and 24.32 g of a 30% strength solution of sodium methylate in methanol (=0.135 mol of NaOCH$_3$) were then added dropwise at a rate such that the temperature of the reaction mixture during the dropwise addition was constantly 65° C.+/–2° C.

When the dropwise addition had ended, the mixture was stirred for a further 5 minutes.

Example 8 (comparison example not according to the invention)

Example 7 was repeated, but without addition of calcium oxide.

Example 9 (according to the invention)

Example 7 was repeated, but instead of 10 g (0.18 mol) of CaO, 7.18 g (0.18 mol) of solid MgO were used.

Examples 10 and 11 (according to the invention)

Example 7 was repeated, but instead of 10 g of CaO, 13.2 g (0.18 tool) of finely powdered Ca(OH)$_2$ (Example 10) or 10.4 g (0.18 mol) of solid Mg(OH)$_2$ (Example 11) were used. The Ca(OH)$_2$, Mg(OH)$_2$ and MgO used in Examples 9 to 11 were in each case anhydrous.

Example 12 (according to the invention)

540.7 g (4.815 mol) of dimethyl phosphite, 320 g (4.5 mol) of acrylamide and 10 g (0.18 mob of solid calcium oxide (CaO) were initially introduced into a reaction vessel. The oxygen content in the reaction vessel was reduced to 7% by weight at room temperature by partial evacuation and subsequent introduction of nitrogen. The mixture was then stirred at room temperature for 90 minutes. The temperature was increased in stages in the course of 2 hours, until the temperature of the reaction mixture was 80° C. The mixture was stirred at an internal temperature of 80° C. for 2 hours and then cooled to an internal temperature of 55° C. 24.32 g of 30 % strength NaOCH$_3$ solution in methanol (=0.135 mol of NaOCH$_3$) were added dropwise such that the reaction mixture was kept at 65° C. It was then stirred at 65° C. for a further 5 minutes.

In all the examples, maintenance of the maximum temperature of the reaction mixture was controlled by a corresponding slow rate of dropwise addition. This resulted in the dropwise addition of the NaOCH$_3$ solution in each case taking several hours.

The dimethyl phosphite and acrylamide used in the examples described above were of technical quality, the purity being in each case about 98%. The acrylamide contained less than 1% by weight of water. In the case of acrylamide, the amounts given in the examples relate to pure (100%) acrylamide, and in the case of dimethyl phosphite they relate to the product of 98% purity.

The content of free acrylamide and of addition product was determined in each of the reaction mixtures obtained in Examples 7 to 12 by means of high pressure liquid chromatography (HPLC). The addition product (dimethylphosphonopropionamide, $(CH_3O)_2P(O)CH_2CH_2CONH_2$) corresponds to the formula (I) given above and in claim 1, where $R^1=R^2=CH^3$, X=H and Y=—$CONH_2$.

The results obtained are shown in the following table:

| Example No. | Content of addition product (% by weight) in the reaction product | Content of free acrylamide (% by weight) in the reaction product |
|---|---|---|
| 7 | 89.0 | 0.17 |
| 8 | 47.8 | 18.3 |
| 9 | 92.1 | 0.2 |
| 10 | 66.7 | 9.6 |
| 11 | 74.7 | 5.9 |
| 12 | 91.0 | 0.05 |

The values for the content given in the above table are % by weight, based on the total amount of reaction product.

The results show that better results are obtained with Examples 7 and 9 to 12 according to the invention than with Comparison Example 8.

We claim:

1. A process for the preparation of a phosphono compound of the formula (I)

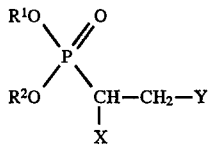

by reaction of a phosphite of the formula (II)

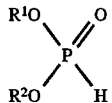

with a compound containing a carbon-carbon double bond, of the formula (III)

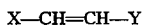

in which $R^1$ and $R^2$, independently of one another, are an unsubstituted phenyl radical or alkyl radical having 1 to 4 carbon atoms or a phenyl radical or alkyl radical having 1 to 4 carbon atoms which is substituted by one or more chlorine atoms or bromine atoms, in which X is hydrogen or a methyl group and in which Y is —$COOR^1$, —$CONH_2$, —$CONHR^1$, —$CONR^1_2$ or —$C\equiv N$, wherein the reaction is carried out both in the presence of a basic catalyst of the formula $MOR^1$, in which M is an alkali metal, and $R^1$ has the abovementioned meaning, and in the presence of a halide, oxide or hydroxide of a divalent metal.

2. A process as claimed in claim 1, wherein a compound of the formula (II) in which $R^1$ and $R^2$ independently of one another are each a methyl or ethyl group is employed.

3. A process as claimed in claim 1, wherein acrylamide is employed as the compound of the formula (III).

4. A process as claimed in claim 1, wherein an alkaline earth metal chloride, alkaline earth metal bromide, alkaline earth metal oxide or alkaline earth metal hydroxide is employed as the halide, oxide or hydroxide of a divalent metal.

5. A process as claimed in claim 1, wherein the halide, oxide or hydroxide of a divalent metal is chosen from the group consisting of magnesium chloride, magnesium oxide, magnesium hydroxide, calcium oxide and calcium hydroxide.

6. A process as claimed in claim 1, wherein essentially anhydrous products are used for the reaction.

7. A process as claimed in claim 1, wherein the reaction is carried out with amounts of starting compounds such that 0.95 to 1.07 mol of phosphite of the formula (II) are employed per mole of compound of the formula (III), these quantities relating to anhydrous and solvent-free products.

8. A process as claimed in claim 1, wherein 0.01 to 0.1 mol of basic catalyst of the formula $MOR^1$ and either 0.001 to 0.05 mol of a halide of a divalent metal or 0.001 to 0.15 mol of an oxide or hydroxide of a divalent metal are employed per mole of compound of the formula (III), all these quantities relating to anhydrous and solvent-free products.

* * * * *